United States Patent [19]

Dinizo et al.

[11] Patent Number: 4,868,333
[45] Date of Patent: Sep. 19, 1989

[54] PRODUCTION OF 2-NITRO-4-TRIFLUOROMETHYLBENZOIC ACID

[75] Inventors: Stephen E. Dinizo, San Lorenzo; Richard D. Gless, Jr., Oakland, both of Calif.

[73] Assignee: ICI Americas Inc., Wilmington, Del.

[21] Appl. No.: 121,694

[22] Filed: Nov. 16, 1987

[51] Int. Cl.$^4$ ............................................. C07C 45/42
[52] U.S. Cl. .................................................... 562/438
[58] Field of Search ........................ 562/438, 443, 493

[56] References Cited

U.S. PATENT DOCUMENTS

| | | | |
|---|---|---|---|
| 3,009,942 | 11/1961 | Klein et al. | 562/492 |
| 3,391,186 | 7/1968 | Thominet et al. | 562/493 |
| 3,542,822 | 11/1970 | Starks | 562/493 |
| 4,307,113 | 12/1981 | Anderson | 514/535 |

OTHER PUBLICATIONS

Hauptschein et al., J.A.C.S., vol. 76, pp. 1051–1054, (1954).
Kalir et al., Israel J. of Chem., vol. 4, pp. 155–159, (1966).

*Primary Examiner*—James H. Reamer
*Attorney, Agent, or Firm*—Joel G. Ackerman; Denis A. Polyn

[57] ABSTRACT

2-Nitro-4-trifluoromethylbenzoic acid is produced by hydrolysis of 2-nitro-4-trifluoromethylbenzonitrile in the presence of relatively concentrated hydrochloric or hydrobromic acid under reflux temperature.

5 Claims, No Drawings

PRODUCTION OF 2-NITRO-4-TRIFLUOROMETHYLBENZOIC ACID

The subject compound is an intermediate in the production of pesticides. One method described in the literature for its production involves the hydrolysis of the corresponding cyano compound:

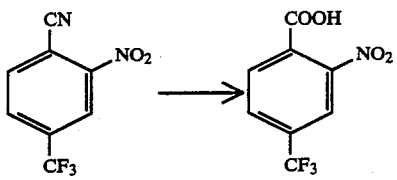

in Hauptschein et al., *J.A.C.S.*, Vol. 76, pp. 1051–1054 (1954). In that work, hydrolysis was conducted using 55% sulfuric acid at 165° C. and 70% sulfuric acid at 190°. However, in the latter case, the main product was 2-nitroterephthalic acid:

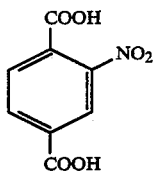

and even when operating with the lower concentration sulfuric acid, this substance was found as a by-product in undesirable quantities.

It would be desirable to produce the subject benzoic acid with little or no terephthalic acid impurity.

SUMMARY OF THE INVENTION

2-Nitro-4-trifluoromethylbenzoic acid is produced from the corresponding benzonitrile by hydrolysis with relatively concentrated hydrochloric or hydrobromic acid at reflux temperature.

DETAILED DESCRIPTION OF THE INVENTION

According to this invention, the subject compound 2-nitro-4-trifluoromethyl benzoic acid is obtained by hydrolysis of the corresponding nitrile according to the reaction

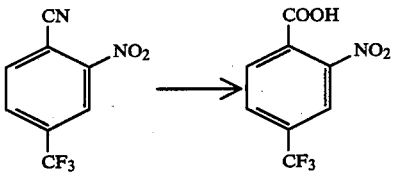

employing as the hydrolyzing agent relatively concentrated aqueous hydrochloric or hydrobromic acid. The activity of these acids in hydrolyzing this nitrile is surprising inasmuch as other acids, such as dilute hydrochloric and phosphoric acids, have been found by us as not effecting this hydrolysis while the use of sulfuric acid, as mentioned above, results in production of some by-product 2-nitroterephthalic acid and in addition generally requires higher reaction temperatures.

The term "relatively concentrated" refers to a concentration which in the case of hydrochloric acid varies from about 25 to about 36%, and for hydrobromic acid, from about 30 to about 48%, both by weight. In general it is preferred to use either acid in the most highly concentrated form.

For hydrobromic acid, the reaction may be conducted using constant boiling aqueous acid (48% concentration) and can be conducted at reflux temperature (about 125° C.). Under these conditions the time required for hydrolysis is between 24 and 36 hours. The product benzoic acid can be recovered from the reaction product by cooling and recrystallizing precipitated solid with an appropriate solvent such as 1,2-dichloroethane or a mixture of toluene and cyclohexane. (The remainder of the precipitated solids appears to be primarily ammonium bromide).

When using hydrochloric acid, the reaction must be conducted under pressure, generally the autogenous pressure of the system, to avoid loss of hydrogen chloride through evaporation. Generally the temperature should be at least about 100° C. to effectuate hydrolysis. At an autogenous pressure of about 180 psi and a temperature of about 125° C., complete hydrolysis usually occurs in 15 hours or less.

The starting material 2-nitro-4-trifluoromethylbenzonitrile may be obtained from a commercial source or prepared according to known techniques such as by the cyanation of a corresponding ring-halogenated benzene.

The conduct of the process according to this invention is illustrated by the following examples.

EXAMPLE 1

A mixture of 493 grams (2.06 moles) 2-nitro-4-trifluoromethylbenzonitrile (90.5% by weight) and 2.89 liters (L) (26 moles) of 48% by weight aqueous hydrobromic acid was placed in a reactor with a stirrer and heated to reflux (pot temperature 126° C.) under nitrogen.

After 29 hours of heating at reflux, gas chromatographic analysis of the reaction mixture showed 91 area percent of the desired acid and less than 0.6 area percent of the starting nitrile.

The mixture was allowed to stand and cooled to ambient temperature. The precipitated solid was collected by filtration and dried at 110° C. to give 615 g of a dark amber solid. A second quantity of 32 g solids was obtained by cooling of the mother liquor. The combined crude solids were slurried with 3.2 L of 1,2-dichloroethane at reflux temperature. The remaining undissolved solid was filtered off and found to consist primarily of ammonium bromide. The dichloroethane mother liquor was cooled to ambient temperature, on which a crystalline solid precipitated. This solid was filtered, washed with dichloroethane, and air dried to produce 395 g (99+% by weight, 1.68 mole) of small yellow needles, analyzed by chromatography and spectroscopy as the desired benzoic acid, melting point 136°–138° C.

The dichloroethane mother liquor was evaporated to a volume of approximately 400 mL, heated to reflux and allowed to cool to ambient temperature. A second quantity of crystals precipitated and was collected as above, producing an additional 50 grams of a dark brown solid, melting point 131°–134° C., again analyzed as the desired benzoic acid (90.6% by weight, 0.19 moles). The overall corrected yield of the benzoic acid, based on the nitrile, was 90.7%. The second crop contained approximately 7% of 2-nitroterephthalic acid (by gas chromatographic area integration), corresponding to an overall yield of less than 1% based on the starting nitrile.

EXAMPLE 2

A mixture of 2-nitro-4-trifluoromethylbenzonitrile (65.0 g, 98.3% by weight, 296 mmol) and 350 mL (413 g, 36% by weight, 4.08 mol) of concentrated hydrochloric acid was sealed in a 750 ml autoclave and heated in an oil bath maintained at 131°–134° C. Because of the extremely corrosive nature of hot concentrated hydrochloric acid, no direct internal temperature measurement could be made during an actual reaction. Blank runs, where the autoclave was charged only with water, had shown that the internal temperature attained under these conditions was 125° C. In the blank runs, the internal temperature stabilized approximately 2 hours after the oil bath. The internal pressure stabilized at 170–180 psig. Heating was maintained for 15 hours after this expected temperature stabilization, and the reactor was then allowed to cool to ambient temperature. The product was collected by filtration, washed with a little cold water and dried in vacuo to afford 63.87 g (98.9% by weight, 269 mmol, corrected yield 90.9%) of an off-white solid: m.p. 135°–138° C. The mother liquor was extracted with three 100 mL portions of 1,2-dichloroethane, which were combined, dried over anhydrous magnesium sulfate and stripped on a rotary evaporator to afford 2.54 g of amber solid: m.p. 105°–108° C. The amber solid contained 86% of the desired product by gas chromatographic area integration. No nitroterephthalic acid was detected.

A similar reaction run for 30 hours at an internal temperature of 150° C. (pressure, 360–370 psig) afforded an 88.2% corrected yield of 2-nitro-4-trifluoromethylbenzoic acid, m.p. 129°–131° C., assay 94.6% by weight. Stripping of the extracts of the mother liquor as above afforded 5.27 g of a brown semi-solid containing 53% of the desired acid and 12% (approximately 1% yield based on the starting nitrile) of nitroterephthalic acid by gas chromatographic area integration.

What is claimed is:

1. A process for the production of 2-nitro-4-trifluoromethylbenzoic acid consisting essentially of hydrolysis of 2-nitro-4-trifluoromethylbenzonitrile in the presence of relatively concentrated hydrochloric or hydrobromic acid.

2. A process according to claim 1 conducted in the presence of between about 25 and about 36% (by weight) aqueous hydrochloric acid, under pressure.

3. A process according to claim 1 conducted in the presence of between about 30 and about 48% (by weight) hydrobromic acid.

4. A process according to claim 3 conducted at reflux temperature.

5. A process according to claim 2 conducted at a temperature of at least about 100° C.

* * * * *